US00PP35690P3

(12) United States Plant Patent
Martin

(10) Patent No.: US PP35,690 P3
(45) Date of Patent: Mar. 12, 2024

(54) CANNABIS PLANT NAMED 'TZT'

(50) Latin Name: *Cannabis sativa*
Varietal Denomination: TZT

(71) Applicant: Umami Worldwide, LLC, Las Vegas, NV (US)

(72) Inventor: Chase Martin, Las Vegas, NV (US)

(73) Assignee: UMAMI WORLDWIDE, LLC, Las Vegas, NV (US)

( * ) Notice: Subject to any disclaimer, the term of this patent is extended or adjusted under 35 U.S.C. 154(b) by 0 days.

(21) Appl. No.: 17/950,089

(22) Filed: Sep. 21, 2022

(65) Prior Publication Data

US 2023/0093796 P1 Mar. 23, 2023

Related U.S. Application Data

(60) Provisional application No. 63/247,287, filed on Sep. 22, 2021.

(51) Int. Cl.
*A01H 5/00* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258, 263.1
CPC ... A01H 5/02; A01H 5/12; A01H 5/00; A01H 6/28
See application file for complete search history.

*Primary Examiner* — June Hwu
(74) *Attorney, Agent, or Firm* — Leonard R. Svensson; Intelink Law Group, P.C.

(57) ABSTRACT

The *Cannabis* cultivar 'TZT' can be briefly characterized by large green and white resin-coated flowers. With very short internodal space and vigorous growth characteristics, this cultivar is able to produce very high yields for both flower and hash production. Little to no purple coloration is observed. Flower clusters have been observed at over 1' of uninterrupted colas.

3 Drawing Sheets

Latin name of the genus and species: *Cannabis sativa.*
Variety denomination: 'TZT'.

BACKGROUND OF THE INVENTION

The present invention relates to a new and distinct *Cannabis* cultivar designated 'TZT'.

TAXONOMY AND NOMENCLATURE

*Cannabis*, more commonly known as marijuana, is a genus of flowering plants that includes at least three species, *Cannabis sativa, Cannabis indica*, and *Cannabis ruderalis* as determined by plant phenotypes and secondary metabolite profiles. In practice however, *Cannabis* nomenclature is often used incorrectly or interchangeably. *Cannabis* literature can be found referring to all *Cannabis* varieties as "*sativas*" or all cannabinoid producing plants as "*indicas*". Indeed, the promiscuous crosses of indoor *Cannabis* breeding programs have made it difficult to distinguish varieties, with most *Cannabis* being sold in the United States having features of both *sativa* and *indica* species.

Human cultivation history of *Cannabis* dates back 8000 years (Schultes, R E., 1970, Random thoughts and queries on the botany of *Cannabis*. Pages 11-38 in: C R B Joyce, and S H Curry eds., THE BOTANY AND CHEMISTRY OF *CANNABIS*. J. & A. Churchill. London, England). Hemp cloth recovered in Europe dates back 6000 years (Small, E, Beckstead, H D, and Chan, A, 1975, The evolution of cannabinoid phenotypes in *Cannabis*, ECONOMIC BOTANY 29(3):219-232). The written record of the pharmacologic properties of *Cannabis* goes back more than 4000 years (Ti, H. 2737 BC. NEI JING SU WEN HUANG TI, Yellow Emperor's Classic on Internal Medicine; referred to without citation in Small et al. 1975 Supra).

The taxonomy and nomenclature of the highly variable genus *Cannabis* (Emboden, W A, 1974, ECONOMIC BOTANY 28(3):304-310; Small, E and Cronquist, A, 1976, TAXON 25(4):405-435; Small E and Cronquist, A, 1977, TAXON 26(1):110; Hillig, K W and Mahlberg, P G, 2004, American Journal of Botany 91(6):966-975), remains in question. This is in spite of the fact that its formal scientific name, *Cannabis sativa* L., assigned by Carolus Linneaus (Linnaeus, C, 1753, SPECIES *PLANTARUM,* 2:1027, Salvius, Stockholm, Facsimile edition, 1957-1959, Ray Society, London, U.K.), is one of the oldest established names in botanical history and is still accepted to this day. Another species in the genus, *Cannabis indica* Lam. was formally named somewhat later (de Lamarck, J B, 1785, ENCYCLOPEDIE METHODIQUE DE BOTANIQUE, 1(2):694-695), but is still very old in botanical history. In 1785, Jean-Baptiste Lamarck published a description of a second species of *Cannabis*, which he named *Cannabis indica*. Lamarck based his description of the newly named species on plant specimens collected in India. *C. indica* was described as relatively short, conical, and densely branched, whereas *C. sativa* was described as tall and laxly branched (Schultes R. E. et al, 1974, Harvard University Botanical Museum Leaflets, 23:337-367). *C. indica* plants were also described as having short, broad leaflets whereas those of *C. sativa* were characterized as relatively long and narrow (Anderson L. C., 1980, Harvard University Botanical Museum Leaflets, 28:61-69). *C. indica* plants conforming to Schultes' and Anderson's descriptions may have originated from the Hindu Kush mountain range. Because of the often harsh and variable (extremely cold winters, and warm summers) climate of those parts, *C. indica* is well-suited for cultivation in temperate climates.

Three other species names were proposed in the 1800s to distinguish plants with presumably different characteristics (*C. macrosperma* Stokes, *C. chinensis* Delile, *C. gigantean* Vilmorin), none of which are accepted today, although the epithet "*indica*" lives on as a subspecies of *C. sativa* (*C. sativa* ssp. *indica* Lam., Small and Cronquist 1976 Supra).

In the 20th century, two new names were added to the 50 liturgy of proposed *Cannabis* species: *C. ruderalis* Janischevsky and a hybrid, x *C. intersita* Sojak. (Small, E, Jui, P Y, and Lefkovitch, L P, 1976, SYSTEMATIC BOTANY 1(1):67-84; Small and Cronquist 1976 Supra). Further, numerous names have been proposed for horticultural variants of *Cannabis* but as of 1976, "very few of these have been validly published as formal taxa under the International Code of Botanical Nomenclature" (Small and Cronquist 1976 Supra). Moreover, other recent work continues to focus on higher-order evolutionary relationships of the genus. *Cannabis* has been variously ascribed as belonging to mulberry family (Moraceae) (Engler, H G A, Ulmaceae, Moraceae and Urticaceae, pages 59-118 in: A. Engler and K. Prantl eds., 1889, DIE NATURLICHEN PFLANZENFAMILIEN 3(1). W. Engelmann, Leipzig, Germany; Judd, W S, Sanders, R W, and Donoghue, M J, 1994, HARVARD PAPERS IN BOTANY 5:1-51; Humphries, C J and Blackmore, S, A review of the classification of the Moraceae, pages 267-277 In: Crane and Blackmore 1989 id.); nettle family (Urticaceae) (Berg, C C, Systematics and phylogeny of the Urticales, pages 193-220, in: P. R. Crane and S. Blackmore eds., 1989, EVOLUTION, SYSTEMATIC, AND FOSSIL HISTORY OF THE HAMAMELIDAE, VOL. 2, HIGHER HAMAMELIDAE, Clarendon Press, Oxford, U.K.); and most recently in its own family with hops (*Humulus*), Cannabaceae, or hemp family (Sytsma, K J, et al, 2002, AMERICAN JOURNAL OF BOTANY 89(9): 1531-1546). While the work of Small and Cronquist 1976 Supra, seemed to effectively confine the genus to a single species with 2 subspecies (*C. sativa* s., *C. s. indica*), each with two varieties (*C. s.* s. var. *sativa, C. s.* s. var. *spontanea; C. s.* i. var. *indica, C. s.* i. var. *Kafiristanica*) largely on the basis of chemotaxonomy and interfertility of all forms, more recent work (Sytsma et al. 2002 Supra), proposes a two-species concept, resurrecting the binomial *C. indica* Lam. Since Sytsma et al. (2002) provides no key for discriminating between the species, the dichotomous key of Small and Cronquist (1976), which accounts for all forms in nature, whether wild or domesticated, is preferred to classify the characteristics of the plants.

BRIEF SUMMARY OF THE INVENTION

The present invention relates to a new and distinct *Cannabis* cultivar designated 'TZT'.

'TZT' is a proprietary hybrid cultivar. The mother is a uniquely vigorous and fast-growing phenotype found by crossing the Oregon French Toast and the PNW Cookies and Cream. The female parent is called Stuffed French Toast or SFT for short. The father is the proprietary breeder stud 'Zuchi' (U.S. Plant patent application Ser. No. 17/950,084). A single plant was selected from a batch of over 500 seeds. It was grown indoors in a fully maintained climate-controlled *Cannabis* cultivation facility in Los Angeles, California.

'TZT' unlike its parent Stuffed French Toast, expresses the distinct ripple wave leaf type and has a much higher concentration of anthocyanins present in both the leaves and stems as well as the harvested flowers. The scent and flavor of the plant is distinct and unique (distinguished from the male parent 'Zuchi' and related known cultivars, such as co-pending plant patent applications for 'AFZ' (application Ser. No. 17/950,086) or 'ZLT' (application Ser. No. 17/950,091), and having notes of gasoline, black pepper, white truffle oil, lavender and non-descript solvents.

'TZT' produces large green and white resin-coated flowers. With very short internodal space and vigorous growth characteristics, this cultivar is able to produce very high yields for both flower and hash production. Little to no purple coloration is observed. Flower clusters have been observed at over 1' of uninterrupted colas.

It is a very hardy plant that is resistant to thrips, aphids, and powdery mildew while able to yield 500-800 grams/m2 in a sea-of-green style growth. A Sea of Green describes growing many plants together to form a continuous canopy. As opposed to growing individual large plants to fill a space, this method groups smaller plants tightly together while maintaining a uniform appearance. The below numbers are the result of 1 selected phenotype from a population of only 10 seeds.

The cannabinoids and terpene analysis are from the dry flower of the selected plant. The method used was High-performance liquid and gas chromatography, otherwise known as HPLC and GCMS. The standard analytical method for these compounds.

Total Cannabinoids: 30.6% @ 9.4% Moisture Content
THCA: 28.6%
D9 THC: 0.327%
CBGA: 1.41%
CBG: 0.198%
Terpenes 1.932944%
Guaiol: 0.0127%
Nerolidol 2: 0.000234%
Alpha-Humulene: 0.541%
Beta-Caryophyllene: 0.164%
Linalool: 0.279%
Terpinolene: 0.00323%
Ocimene 2: 0.0148%
d-Limonene: 0.656%
Ocimene 1: 0.00108%
beta-Pinene: 0.103%
beta-Myrcene: 0.5567%
Camphene: 0.0152%
Alpha Pinene: 0.0736%

DETAILED BOTANICAL DESCRIPTION

Figure 1:
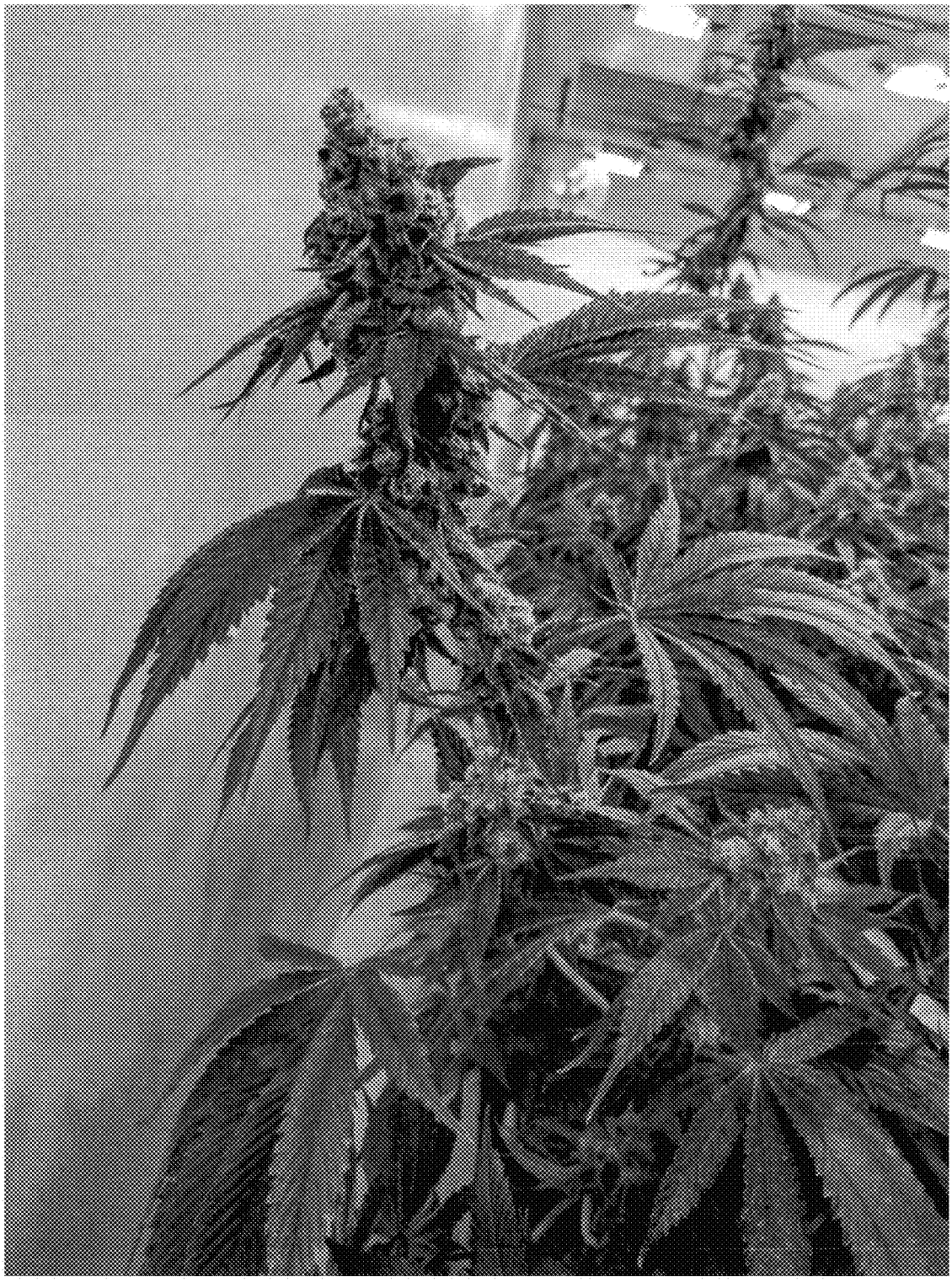
FIG. 1 is a view of a 'TZT' plant including several flower clusters.
Figure 2:
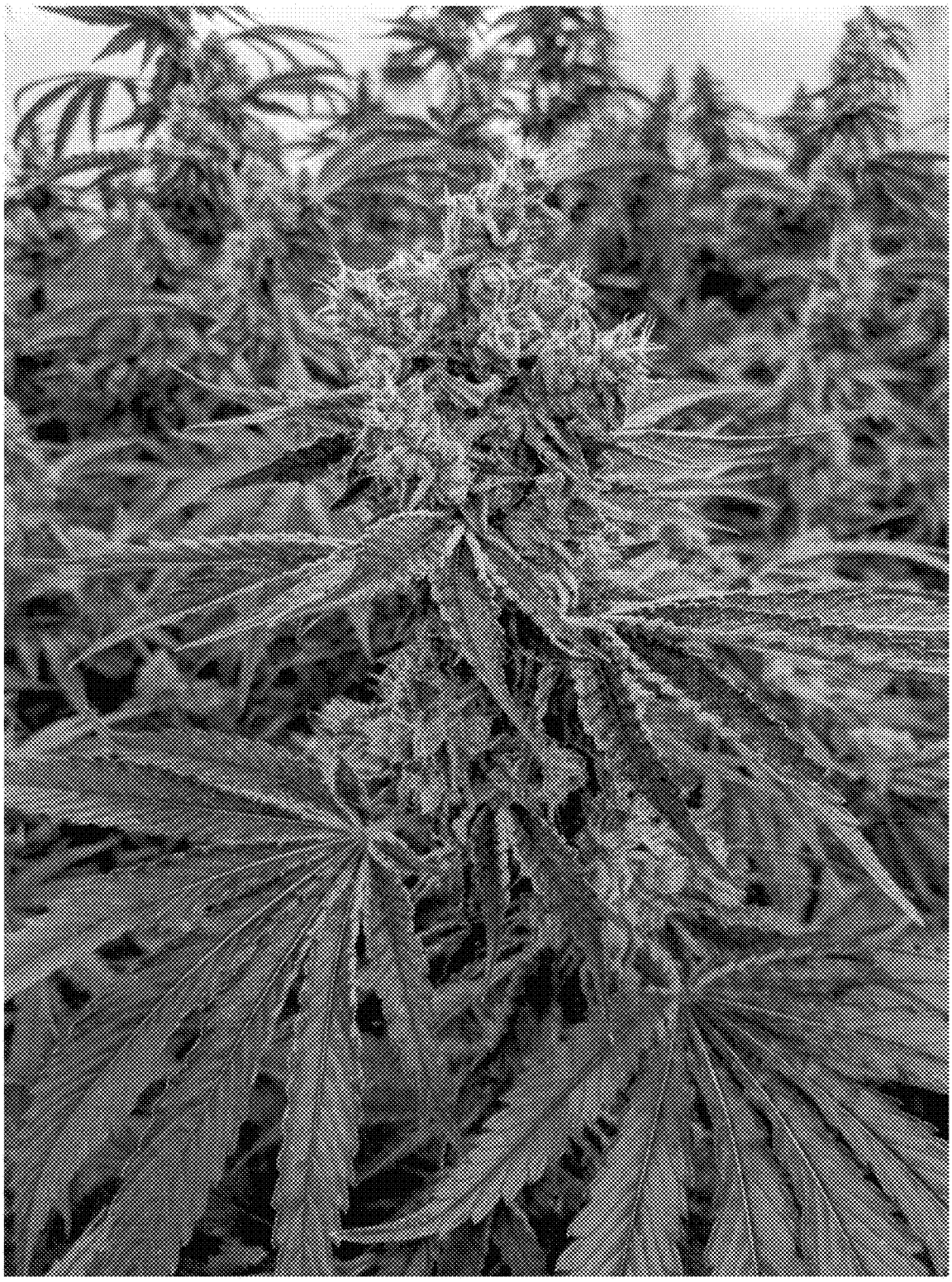
FIG. 2 is a close-up view of several 'TZT' flower clusters on a growing 'TZT' plant.
Figure 3:
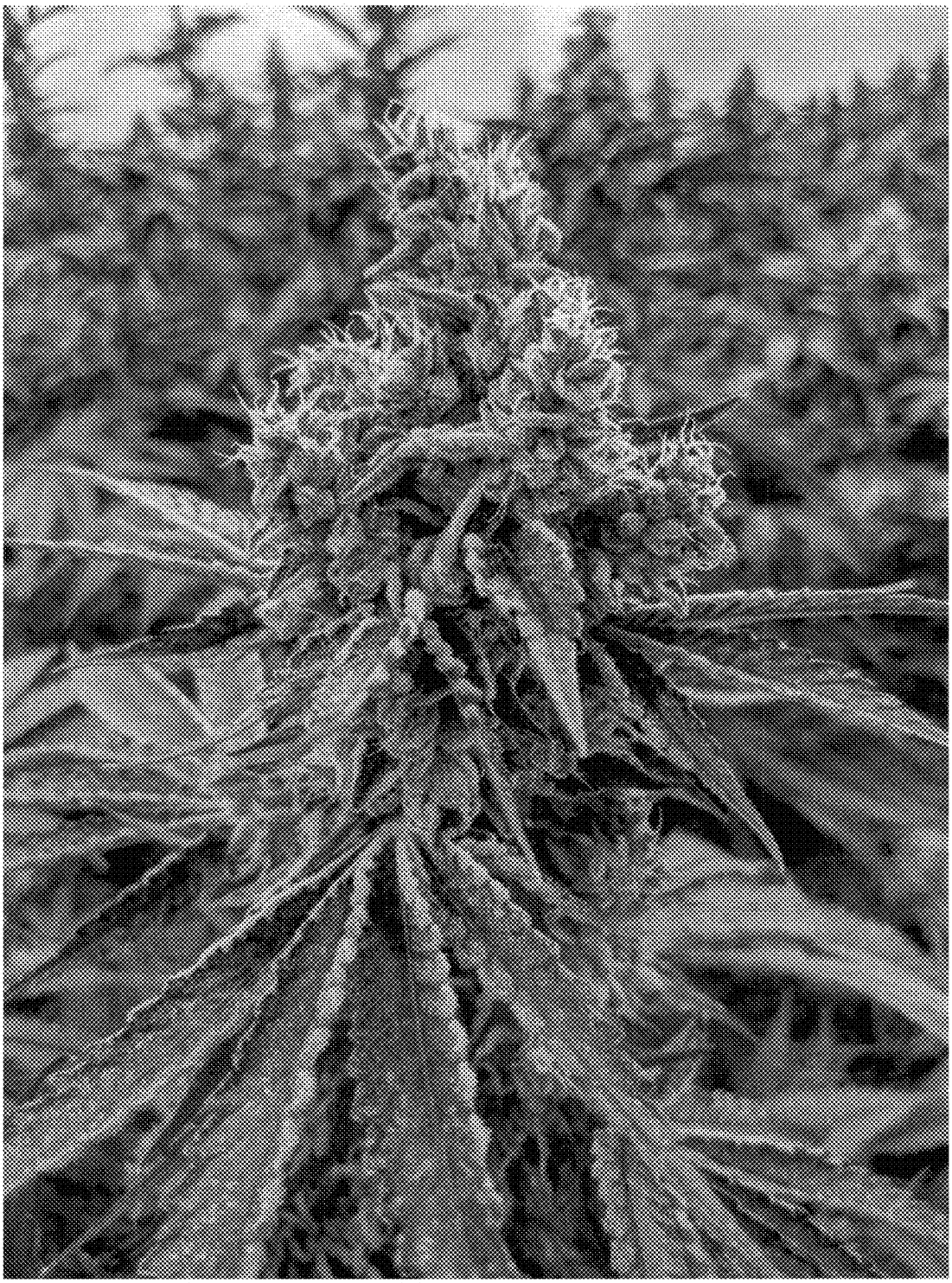
FIG. 3 is a close-up view of a 'TZT' flower cluster on a growing 'TZT' plant.

'TZT' has not been observed under all possible environmental conditions, and the phenotype may vary significantly with variations in environment. The following observations, measurements, and comparisons describe this plant as grown at Mentone, Calif., when grown in the greenhouse, nursery or field, unless otherwise noted. The new plant reproduces true to type with all of the characteristics, as herein described, and is asexually propagated via meristem Tissue Culture and Clonal propagation in Los Angeles California.

The color chart referenced is standard hexadecimal Web Pantone Color Chart well known to those of ordinary skill in Internet web site design.

THE PLANT

Type (life form and habit). Herbaceous tap-rooted annual.

*Height*.—The average height can be modified depending on the volume of growing media and the irrigation frequency. In a 6×6×6 rockwool cube, being fed 1500-2000 ml per day a plant will average around 75" in height. The selected plant is grown in clusters with 9-12 plants per 16-24 ft2. 'TZT' is an incredibly vigorous plant, clones will take between 6-10 days to show roots and will reach a height of around 20-26" after only 17-20 days.

*Leaves*.—The leaves are large and broad. The central leaflet is very broad, and each leaf overlaps the others and does not allow light to penetrate. They can be 8-12" long and have a total width of 8-10". The leaf is heavy gloss and shines bright in the sun or under HID or LED lighting. The leaf ridges are very deep and wavy, the leaves do not lie flat but are shaped like a soundwave with equal parts up and down. The trichomes are mostly tall capitate stalked and are wet and greasy to the touch, releasing a heavy aroma of gasoline, black pepper, white truffle oil, lavender and solvent. The average number of leaflets is between 5-13 depending on the total plant size and health. The upper leaf surface is dark green PMS 356 with the lower surface a light green PMS 374.

*Petioles*.—The petioles are abnormally long, typically 4-6" long and 0.2-0.4" in diameter. The longer and older petioles will show anthocyanin production starting closer to the stem and moving out toward the leaf rachis. Trichomes are glandular with capitate stalked visible and bulbous trichomes and capitate-sessile trichomes are present all around. Petioles are dark green PMS 369 with purple anthocyanin streaking PMS 525.

*Stipules*.—Found at each node and are usually between 0.22-0.25" in length. They are medium to light green PMS 360-368 (the older the darker) and spear-shaped and accompanied by white pistils regardless of the light cycle or season.

*Stem*.—The stem shape is a large oval that has a zig-zag pattern as it grows (like most Zuchi progeny). Each node will begin to grow in the opposite direction of the previous node at the same growth angle. The internodal spacing is very short 1-2.5" and compact. The stem is round and can reach a diameter of 1.25-1.5" when grown with a shallow groove depth and thick pith presence (full stems). Stem color is a medium green PMS 557. There are capitate and bulbous visible trichomes growing on the stem.

*Flower*.—The flowers are rounded and bulbous at the base and emerge outward into sharp points with many sharp points emerging outward like a pine-cone. The % of male vs female plants was approximately 55% female and 45% males in the selection process. There was <5% hermaphrodite expression from seed and after taking clones, the hermaphroditic expression was not seen again. The flowers are arranged in a spiral pattern up the stem like Brussels sprouts with each flower being fully formed and not contributing to a homogeneous "cola" shape. The flowers are dark green PMS 357 with dark purple streaking PMS 525 but look frosted white due to the heavy presence and density of the large trichomes on every square millimeter of the flower. The fragrance is that of gasoline, black pepper, white truffle oil, lavender, and solvent; a very noxious and intense smell that is overwhelming.

*Bract*.—The bract is medium to dark green PMS 576 and 0.16" in diameter and 0.22-0.25" in length with 2 stigmas emerging from the center. They are covered with capitate-stalked trichomes and house bulbous and capitate-sessile trichomes throughout.

*Bracteoles*.—Usually between 0.1-0.115" in length. They are slender spear-shaped and medium-dark green color PMS 576.

*Stigma*. Bright yellow PMS 603 and can reach up to 1.5 mm in size during the first 3 weeks of the flowering stage.

Seeds. The seeds are round/oval in shape. The weight is high and fully mature seeds are dark gray/brown PMS 1405 with weak marbling that can only be noticed with close examination.

Classification. Cultivars of *Cannabis sativa*.

*Market use*.—Market use for this product is medical and recreational *Cannabis* flower as well as extracts and infused goods. Individual plants grown with the above methods yield an average total plant wet weight of 2900-3200 g at harvest resulting in a dry flower weight of 150-200 grams.

*Growth conditions*.—The plants are grown and are meant to be grown in a tightly controlled environment. They have been able to withstand temperatures above 105 degrees F. with 95% RH, as well as a RH of as low as 20%. Recent testing has shown that TZT is capable of thriving in a greenhouse with temperatures as low as 40 F with 85-95% RH. This cultivated line possesses intoxicating properties, and the Subspecies *sativa* and its varieties (var. *sativa* and *spontanea*) are eliminated from consideration.

All references cited in this specification, including but not limited to patent publications and non-patent literature, and references cited therein, are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A new and distinct variety of *Cannabis* plant, named 'TZT', substantially as illustrated and described herein.

* * * * *